(12) United States Patent
Lele et al.

(10) Patent No.: US 9,974,549 B2
(45) Date of Patent: May 22, 2018

(54) SURGICAL ACCESS TOOLS, GUIDE INSTRUMENTS AND ACCESSORIES FOR SUBCHONDRAL TREATMENT OF BONE

(71) Applicant: ZIMMER KNEE CREATIONS, INC., Exton, PA (US)

(72) Inventors: Meenal N. Lele, Philadelphia, PA (US); Christopher D. Mandeen, West Chester, PA (US); Shaun B. Hanson, West Chester, PA (US)

(73) Assignee: ZIMMER KNEE CREATIONS, INC., Exton, PA (US)

( * ) Notice: Subject to any disclaimer, the term of this patent is extended or adjusted under 35 U.S.C. 154(b) by 312 days.

(21) Appl. No.: 14/775,965

(22) PCT Filed: Mar. 13, 2014

(86) PCT No.: PCT/US2014/025444
§ 371 (c)(1),
(2) Date: Sep. 14, 2015

(87) PCT Pub. No.: WO2014/159913
PCT Pub. Date: Oct. 2, 2014

(65) Prior Publication Data
US 2016/0022284 A1 Jan. 28, 2016

Related U.S. Application Data

(60) Provisional application No. 61/785,821, filed on Mar. 14, 2013.

(51) Int. Cl.
*A61B 17/17* (2006.01)
*A61B 17/84* (2006.01)
*A61B 17/16* (2006.01)
*A61B 17/34* (2006.01)

(52) U.S. Cl.
CPC ............ *A61B 17/17* (2013.01); *A61B 17/162* (2013.01); *A61B 17/1764* (2013.01);
(Continued)

(58) Field of Classification Search
CPC .. A61B 17/17; A61B 17/1725; A61B 17/1764
See application file for complete search history.

(56) References Cited

U.S. PATENT DOCUMENTS 8,062,364 B1 11/2011 Sharkey et al.
2002/0193801 A1 12/2002 Marchione et al.
(Continued)

FOREIGN PATENT DOCUMENTS

FR 2716364 A1 8/1995
WO WO-2011008739 A2 1/2011
(Continued)

OTHER PUBLICATIONS

"International Application Serial No. PCT/US2014/025444, International Search Report dated Jun. 24, 2014", 3 pgs.
(Continued)

*Primary Examiner* — Christian Sevilla
(74) *Attorney, Agent, or Firm* — Schwegman Lundberg & Woessner, P.A.

(57) ABSTRACT

One embodiment disclosed provides a guide instrument for controlling the depth and trajectory of a surgical access device into a bone.

19 Claims, 4 Drawing Sheets

(52) U.S. Cl.
CPC ...... *A61B 17/3403* (2013.01); *A61B 17/3472* (2013.01); *A61B 17/848* (2013.01); *A61B 17/1675* (2013.01); *A61B 2017/3409* (2013.01)

(56) References Cited

U.S. PATENT DOCUMENTS

| | | | |
|---|---|---|---|
| 2007/0088362 A1* | 4/2007 | Bonutti | A61B 17/0218 606/99 |
| 2010/0030218 A1* | 2/2010 | Prevost | A61B 17/1655 606/80 |
| 2011/0125156 A1 | 5/2011 | Sharkey et al. | |
| 2011/0125157 A1 | 5/2011 | Sharkey et al. | |
| 2013/0261650 A1 | 10/2013 | Hanson et al. | |

FOREIGN PATENT DOCUMENTS

| | | |
|---|---|---|
| WO | WO-2011063281 A1 | 5/2011 |
| WO | WO-2014159913 A1 | 10/2014 |

OTHER PUBLICATIONS

"International Application Serial No. PCT/US2014/025444, Written Opinion dated Jun. 24, 2014", 4 pgs.

"European Application Serial No. 14716489.1, Communication Pursuant to Article 94(3) EPC dated Sep. 11, 2017", 4 pgs.

"European Application Serial No. 14716489.1, Communication Pursuant to Article 94(3) EPC dated Nov. 24, 2016", 5 pgs.

"European Application Serial No. 14716489.1, Response Filed Apr. 4, 2017 Communication Pursuant to Article 94(3) EPC dated Nov. 24, 2016", 11 pgs.

"European Application Serial No. 14716489.1, Response filed May 16, 2016 to Communication pursuant to Rules 161(1) and 162 EPC dated Nov. 5, 2015", 8 pgs.

"International Application Serial No. PCT/US2014/025444, International Preliminary Report on Patentability dated Sep. 24, 2015", 6 pgs.

* cited by examiner

FIG. 6

SURGICAL ACCESS TOOLS, GUIDE INSTRUMENTS AND ACCESSORIES FOR SUBCHONDRAL TREATMENT OF BONE

CLAIM OF PRIORITY

This application is a U.S. National Stage Filing under 35 U.S.C. 371 from International Application No. PCT/US2014/025444, filed on 13 Mar. 2014, and published as WO 2014/159913 A1 on 2 Oct. 2014, which claims the benefit under 35 U.S.C. § 119(e) of U.S. Provisional Patent Application Ser. No. 61/785,821, filed on Mar. 14, 2013, which applications are incorporated by reference herein in their entirety.

FIELD

The present invention relates to medical instruments and accessories, and more particularly, to surgical access tools, guide instruments and accessories for the injection or extraction of materials into or out of a patient's body. Even more particularly, these access tools, guide instruments and accessories can cooperate with other known surgical instruments, including power tools, for subchondral treatment of bone. In particular, the guide instrument includes a depth control guide instrument that cooperates with access pins or needles for targeting a subchondral region of bone.

BACKGROUND

Many medical procedures or treatments require internal access into the patient's body. Surgical access into the body may sometimes involve a working channel for the insertion of tools for the injection or removal of materials into or out of a desired site within the body. In a majority of cases, an access device, such as a cannula, is used to provide this working channel. For example, in many surgical bone treatments, a portal to inject directly into the bone is employed. This portal is conventionally created with a standard trocar and cannula. Generally, before or during the process of removing the trocar, the surgeon will manually drive, either by pushing, twisting, or a combination of both, the cannula into the bone. The residing cannula provides a clear path into the bone for effecting treatment.

Problems arise, however, when the cannula or trocar must overcome a large resistive force as it is being inserted into the bone. When the force is finally overcome, the cannula or trocar plunges too far forward. Another problem is created during bone treatments when manually twisting the cannula into bone creates an oval cavity in the cortical bone and negates the seal. These issues can lead to damage of cancellous/cortical bone, or an incomplete fill with extravasations.

It would therefore be desirable to provide the necessary tools and instruments to allow a powered tool to drive an access device such as a cannula, pin, needle, or other known injection or extraction portal, directly into the patient's body. It would also be desirable to provide surgical access instruments and systems that allow the surgeon with more control to create the working channel for medical treatments. It would be even more desirable to provide these instruments and systems with better depth control, alignment control, and ease of use.

SUMMARY

The present disclosure provides embodiments for a guide instrument for controlling the depth and trajectory of a surgical access device into a bone.

In one embodiment, a guide instrument for guiding an access device into a bone of a joint is provided. This particular instrument comprises a cartridge that includes a main body and a translatable arm that is receivable in a passage in the main body for translating relative to the main body. The translatable arm includes a portal for receiving an access device in alignment with an opening in the main body so that the access device can extend through the portal and the opening in the main body. The guide instrument further includes a probe extending from the translatable arm and a handle extending from the cartridge.

In another embodiment, a guide instrument for targeting an access device into a bone of a joint is provided. The instrument may comprise a cartridge comprising a main body that includes a slot for receiving a movable arm. The arm may include a probe and provide a portal for receiving the access device. This portal may be aligned with an opening in the main body for insertion of the access device therethrough. The instrument further includes a handle extending from the cartridge. The handle can be configured to rest against a patient's body, such as against bone or cartilage. In use, the instrument aligns the access device to a location spaced from the probe and on the bone to be treated (e.g., below the probe).

Such a handle can include means for resting firmly against the patient's leg, optionally with radiopaque markers that can be used to align with the tibia, and an articular probe that indexes and moves slidably with respect to the handle against the leg surface. In addition, the probe mechanism may comprise an open portal and depth control sleeve that is fixed relative to the targeting end of the probe to accept an access device or cannula of fixed length. As the probe tip is indexed and adjusted with respect to the handle at any depth into the joint, the mechanism with portal depth control ensures that the maximum depth of the cannula is referenced and controlled with respect to the probe target end for any given indexed depth position of the probe.

Another embodiment provides a guide system for guiding an access device into a bone. This particular system includes a cartridge and an access device such as a needle or pin having a cannulated section. The cartridge comprises a main body and a translatable arm that is receivable in the main body for translating relative to the main body. The translatable arm includes a portal for receiving the access device in alignment with an opening in the main body. The access device is extendable through the portal and the opening in the main body.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DESCRIPTION OF THE EMBODIMENTS

Methods, devices and instruments for treating joint pain to restore natural joint function and preserving, as much as possible, the joint's articular and cartilage surface are known. Treatments through the joint that violate the articular and cartilage surface often weaken the bone and have unpredictable results. Rather than focusing on treatment of pain through the joint, alternative treatments that diagnose and treat pain at its source in the subchondral region of a bone of a joint to relieve the pain are provided. Pain associated with joints, especially osteoarthritic joints, can be correlated to bone defects or changes at the subchondral level rather than, for example, the severity of osteoarthritic progression or defects at the articular surface level. In particular, bone defects, such as bone marrow lesions, edema, fissures, fractures, hardened bone, etc. near the joint surface lead to a mechanical disadvantage and abnormal stress distribution in the periarticular bone, which may cause inflammation and generate pain. By altering the makeup of the periarticular bone (which may or may not be sclerotic) in relation to the surrounding region, it is possible to change the structural integrity of the affected bone and restore normal healing function, thus leading to a resolution of the inflammation surrounding the defect.

Treatment of the bone by mechanical and biological means to restore the normal physiologic stress distribution, and restore the healing balance of the bone tissue at the subchondral level, is a more effect way of treating pain than conventional techniques. That is, treatment can be effectively achieved by mechanically strengthening or stabilizing the defect, and biologically initiating or stimulating a healing response to the defect. Methods, devices, and systems for a subchondral procedure that achieve these goals are disclosed in co-owned U.S. Pat. No. 8,062,364 entitled "OSTEOARTHRITIS TREATMENT AND DEVICE" as well as in co-owned and co-pending U.S. Patent Application Publication Nos. 2011/0125156 entitled "METHOD FOR TREATING JOINT PAIN AND ASSOCIATED INSTRUMENTS" and 2011/0125157 entitled "SUBCHONDRAL TREATMENT OF JOINT PAIN," both of which were filed on Nov. 19, 2010, the contents of which are incorporated by reference in their entirety. This subchondral procedure, and its associated devices, instruments, etc. are also marketed under the registered trademark name of SUBCHONDROPLASTY™. The SUBCHONDROPLASTY™ procedure is a response to a desire for an alternative to patients facing partial or total knee replacement.

In general, the SUBCHONDROPLASTY™ or SCP™ technique is intended to both strengthen the bone and stimulate the bone. In an SCP™ procedure, bone fractures or non-unions are stabilized, integrated or healed, which results in reduction of a bone defect, such as a bone marrow lesion or edema. In addition, the SCP™ procedure restores or alters the distribution of forces in a joint to thereby relieve pain. The SCP™ procedure can be performed arthroscopically or percutaneously to treat pain by stabilizing chronic stress fracture, resolving any chronic bone marrow lesion or edema, and preserving, as much as possible, the articular surfaces of the joint. The SUBCHONDROPLASTY™ procedure generally comprises evaluating a joint, for example, by taking an image of the joint, detecting the presence of one or more subchondral defects, diagnosing, which of these subchondral defects is the source of pain, and determining an extent of treatment for the subchondral defect. The technique is particularly suited for treating chronic defects or injuries, where the patient's natural healing response has not resolved the defect. It should be noted, however, that the technique is equally applicable to treatment of defects in the subchondral region of bone where the defect is due to an acute injury or from other violations. Several exemplary treatment modalities for the SCP™ procedure for the different extents of treatment needed can be employed. Accordingly, a medical practitioner may elect to use the techniques and devices described herein to subchondrally treat any number of bone defects, as he deems appropriate.

Detection and identification of the relevant bone marrow lesion or bone marrow edema (BML or BME) can be achieved by imaging, e.g., magnetic resonance imaging (MRI), X-ray, bone scans, manual palpation, chemical or biological assay, and the like. A T1-weighted MRI can be used to detect sclerotic bone, for example. Another example is that a T2-weighted MRI can be used to detect lesions, edemas, and cysts. X-ray imaging may be suitable for early-stage as well as end-stage arthritis. From the imaging, certain defects may be identified as the source of pain. In general, defects that are associated with chronic injury and chronic deficit of healing are differentiated from defects that result, e.g., from diminished bone density. SCP™ treatments are appropriate for a BML or BME that may be characterized as a bone defect that is chronically unable to heal (or remodel) itself, which may cause a non-union of the bone, stress or insufficiency fractures, and perceptible pain. Factors considered may include, among other things, the nature of the defect, size of the defect, location of the defect, etc. For example, bone defects at the edge near the articular surface of periphery of a joint may be often considered eligible for treatment due to edge-loading effects as well as the likelihood of bone hardening at these locations. A bone defect caused by an acute injury would generally be able to heal itself through the patient's own natural healing process. However, in such situations where the bone defect is due to an acute injury and either the defect does not heal on its own, or the medical practitioner decides that the present technique is appropriate, SCP™ treatment can be administered on acute stress fractures, BML or BME, or other subchondral defects, as previously mentioned.

The SCP™ treatment may continue after surgery. In particular, the patient may be monitored for a change in pain scores, or positive change in function. For example, patients are also checked to see when they are able to perform full weight-bearing activity and when they can return to normal activity. Of note, the SCP™ procedure can be revised and thus allows for optional further treatment in the event that a patient requires or desires a joint replacement or other type of procedure. The procedure does not exclude a future joint repair or replacement treatment to be applied, and thus may also be performed in conjunction with other procedures, such as cartilage resurfacing, regeneration or replacement, if desired. In those instances where additional treatment is desired, the SCP™ treated area may remain undisturbed while the additional treatment is performed, such as where cartilage resurfacing is desired. Alternatively, the SCP™ treated area can be removed, and not create an obstacle to the additional treatment, such as where a partial or total joint replacement is desired. Advantageously, the SCP™ treatment may be provided as a first or initial treatment, reserving for the future and possibly forestalling until a later date than otherwise might be the case more invasive treatments such as partial or total joint replacement.

Various surgical treatments to address subchondral defects known as bone marrow lesions have previously been attempted. Between May and November 2008, three (3) surgeries were performed at Riddle Hospital in Media, Pa. in the United States. On May 12, 2008, Dr. Peter F. Sharkey performed a right knee arthroscopy with arthroscopically assisted stabilization of a patient's right knee with a medial tibial plateau fracture. During the procedure, a cannulated bone biopsy needle was placed into the bone under fluoroscopic guidance, and augmentation material was injected. The injected augmentation material was Stryker Orthopedics Hydroset (Bone Substitute Material). The surgeon expressed difficulty in injecting the bone substitute material.

On Oct. 27, 2008, Dr. Steven B. Cohen performed a left knee arthroscopy, partial medial meniscectomy, drilling of osteochondral lesion using retrograde technique, and debridement chondroplasty of patellofemoral chondrosis on a patient's left knee with medial meniscus tear and left knee osteochondral defect with bone marrow lesion of the medial femoral condyle. During the procedure, an Anterior Cruciate Ligament (ACL) portal-creation device was repurposed for this surgery. The tibial probe was placed on the medial femoral condyle, with the tunnel guide secured proximally on the thigh. The surgeon expressed difficulty in positioning and stabilizing the guide. A cannulated pin was placed through the tunnel guide and placed distally into the medial femoral condyle. No implantable material was injected into the bone in this case.

On Nov. 10, 2008, Dr. Steven B. Cohen performed a right knee arthroscopic-assisted repair of a tibial plateau fracture bone marrow lesion with subchondral fracture using bone cement, partial medial and partial lateral meniscectomy to treat medial meniscus tear, and arthroscopic debridement and chondroplasty of medial, lateral, and patellofemoral compartments to treat compartment chondrosis. During the procedure, a guide pin was inserted into the medial tibial plateau, and an endo button drill bit was used to expand the drill hole. One (1) cubic centimeter (cc) of cement was inserted into the bone. A second drill hole was made from below, and a second cubic centimeter (cc) of cement was inserted into the bone.

The experiences gained from these previous surgeries helped to develop the fundamental theories underlying the SUBCHONDROPLASTY™ procedure and the number of treatment modalities, associated devices, instruments and related methods of use for performing the SUBCHONDROPLASTY™ procedure, which are disclosed in the aforementioned publications. These treatment modalities may be used alone or in combination, as will be described in detail below. In one treatment modality, the subchondral bone in the region of the bone marrow lesion or defect can be strengthened by introduction of a hardening material, such as a bone substitute, at the site. The bone substitute may be an injectable calcium phosphate ensconced in an optimized carrier material. In SCP™, the injected material may also serve as a bone stimulator that reinvigorates the desired acute bone healing activity.

For example, polymethylmethacrylate (PMMA) or calcium phosphate (CaP) cement injections can be made at the defect site. PMMA injection may increase the mechanical strength of the bone, allowing it to withstand greater mechanical stresses. CaP cement injection may also increase the mechanical strength of the bone, while also stimulating the localized region for bone fracture repair. In one embodiment, the injection can be made parallel to the joint surface. In another embodiment, the injection can be made at an angle to the joint surface. In yet another embodiment, the injection can be made below a bone marrow lesion. Preferably, the injection is made without disrupting the joint surface.

In another treatment modality, the subchondral bone region can be stimulated to trigger or improve the body's natural healing process. For example, in one embodiment of this treatment modality, one or more small holes may be drilled at the region of the defect to increase stimulation (e.g., blood flow, cellular turnover, etc.) and initiate a healing response leading to bone repair. In another embodiment, after holes are drilled an osteogenic, osteoinductive, or osteoconductive agent may be introduced to the site. Bone graft material, for example, may be used to fill the hole. This treatment modality may create a better load-supporting environment leading to long term healing. Electrical or heat stimulation may also be employed to stimulate the healing process of a chronically injured bone. Chemical, biochemical and/or biological stimulation may also be employed in SCP™. For instance, stimulation of bone tissue in SCP™ may be enhanced via the use of cytokines and other cell signaling agents to trigger osteogenesis, chondrogenesis, and/or angiogenesis to perhaps reverse progression of osteoarthritis.

In yet another treatment modality, an implantable device may be implanted into the subchondral bone to provide mechanical support to the damaged or affected bone region, such as where an insufficiency fracture or stress fracture has occurred. The implant may help create a better load distribution in the subchondral region. In the knees, the implant may support tibio-femoral compressive loads. In addition, the implant may mechanically integrate sclerotic bone with the surrounding healthy bone tissue. The implants may be place in cancellous bone, through sclerotic bone, or under sclerotic bone at the affected bone region. The implant may also be configured as a bi-cortical bone implant. In one embodiment, one side of the implant can be anchored to the peripheral cortex to create a cantilever beam support (i.e., a portion of the implant is inserted into bone but the second end stays outside or near the outer surface of the bone). The implant may be inserted using a guide wire. In one example, the implant may be inserted over a guide wire. In another example, the implant may be delivered through a guide instrument.

The implant may further be augmented with a PMMA or CaP cement injection, other biologic agent, or an osteoconductive, osteoinductive and/or osteogenic agent. The augmentation material may be introduced through the implant, around the implant, and/or apart from the implant but at the affected bone region, such as into the lower region of a bone marrow lesion or below the lesion. For example, the implant may act as a portal to inject the augmentation material into the subchondral bone region.

While each of the above-mentioned treatment modalities may be administered independent of one another, it is contemplated that any combination of these modalities may be applied together and in any order so desired, depending on the severity or stage of development of the bone defect(s). Suitable implantable fixation devices for the surgical treatment of these altered bone regions or bone defects, especially at the subchondral level, are known. These devices and instruments can be use in combination with cements or hardening materials commonly used to repair damaged bone by their introduction into or near the site of damage, either to create a binding agent, cellular scaffold or mechanical scaffold for immobilization, regeneration or remodeling of the bone tissue. As previously stated, treatment of the bone defect at the subchondral level preferably is performed without disrupting the joint surface.

In a healthy joint such as a tibio-femoral joint, the compressive load between the contact bones (i.e., the femur and the tibia) is properly distributed, thus keeping the contact stresses in the cartilage to a reasonably low level. As the cartilage starts to wear out or degenerate locally, the tibio-femoral contact area reduces and starts to get localized at the site of the cartilage defect. The localization of the stresses may also occur due to varus or valgus deformity. Sometimes, the condition may occur because of osteoporosis, where bone becomes weak and is no longer able to support normal loads. This condition leads to higher localized contact stresses in the cartilage, and the subchondral region below the cartilage. Once the stresses reach beyond a certain threshold level, it leads to defects like bone marrow lesions and edema, and perhaps generates knee pain. If the problem persists, the high contact stresses can lead to sclerotic bone formation as well. The presence of sclerotic bone can compromise vascularization of the local area, and also create a mechanical mismatch in the bone tissue. This mismatch may start to expedite degeneration of all parts of the joint leading to increased levels of osteoarthritis.

Pain associated with osteoarthritic joints can be correlated to bone defects or changes at the subchondral level. In particular, bone defects such as bone marrow lesions, edema, fissures, fractures, etc. near the joint surface lead to abnormal stress distribution in the periarticular bone, which may or may not cause inflammation and generate pain. By altering the makeup of the periarticular bone (which may or may not be sclerotic) in relation to the surrounding region, it is possible to change the structural integrity of the affected bone, leading to a resolution of the inflammation. Treatment of the bone in an effort to alter the structural makeup of the affected periarticular bone leads to reduced inflammation and pain has proven to be successful. Over time, restoration of normal physiologic stress distribution can be achieved in load bearing joints such as the hip and knee, and mechanical congruity restored, thereby resulting in healing of the inflammation and reduction or elimination of pain.

One of the benefits offered by the SCP™ procedure is that the procedure allows for optional further treatment in the event that a patient requires or desires a joint replacement or other type of joint pain relieving procedure. The subchondral treatment described herein does not exclude a future joint repair or replacement treatment to be applied, and thus may also be performed in conjunction with other procedures. For example, total knee replacements (TKR) or total knee arthroplasties (TKA), partial knee replacements, arthroscopies, meniscal tear repairs, torn ligament repairs, microfracture treatments, cartilage resurfacing, regeneration or replacement, and other types of joint repairs are combinable with a subchondral treatment to stabilize and enhance the strength of the subchondral bone, either as a prophylactic approach or as a targeted treatment of an existing subchondral defect. In fact, the principles of SCP™ can be applied in a combination of therapies to address a number of problems arising from the disease state, either sequentially or in parallel, at one time or over a duration of time. That is, the SCP™ treatment may be performed intraoperatively along with the other joint treatment, or it may be done postoperatively as an adjunct to the primary joint repair treatment.

For instance, in one example, the SCP™ treatment may continue after surgery. In those patients where additional treatment is desired, the SCP™ treated area may remain undisturbed while the additional treatment is performed, such as where cartilage resurfacing is desired. Alternatively, the SCP™ treated area can be removed, so as not to create an obstacle to the additional treatment, such as where a partial or total joint replacement is desired. Advantageously, the SCP™ treatment may be provided as a first or initial treatment, reserving for the future and possibly forestalling until a later date than otherwise might be the case more invasive treatments such as partial or total joint replacement. In other examples, the SCP™ treatment may be combined other non-surgical treatments such as injections.

In general, the present disclosure provides surgical instruments that are useful to carry out the SCP™ treatment modalities described above, as well as for surgical access in general, including situations where the target location may reside within bone tissue. The embodiments include systems, guide instruments and accessories that allow an access device, such as a cannula, pin, needle, or other known injection or extraction portal, to be power driven directly into the patient. The ability to drive an access device or portal directly into the patient's body using power such as with a standard power drill enables the user to gain better control of the process, such as by reducing the chances of misalignment during insertion, and over-insertion or under-insertion, to name a few examples.

In co-owned and co-pending U.S. patent application Ser. No. 13/854,796, entitled "SURGICAL ACCESS SYSTEMS, INSTRUMENTS AND ACCESSORIES," which was filed on Apr. 1, 2013 and published as U.S. Patent Application Publication No. 2013/0261650, various systems, guide instruments and accessories that allow an access device, such as a cannula, pin, needle, or other known injection or extraction portal, to be power driven directly into the patient are disclosed, the contents of which are herein incorporated by reference in their entirety. These systems, guide instruments and accessories are suitable for use with the depth control guide instrument disclosed herein, and reference shall be made to these systems, guide instruments and accessories from time to time.

Reference will now be made to the figures to illustrate various aspects and embodiments of the present invention. In the following detailed description, numerous specific details are set forth to provide a full understanding of the present invention. It will be apparent, however, to one ordinarily skilled in the art that the present invention may be practiced without some of these specific details. In other instances, well-known structures and techniques have not been shown in detail to avoid unnecessarily obscuring the present invention.

Figure 1:
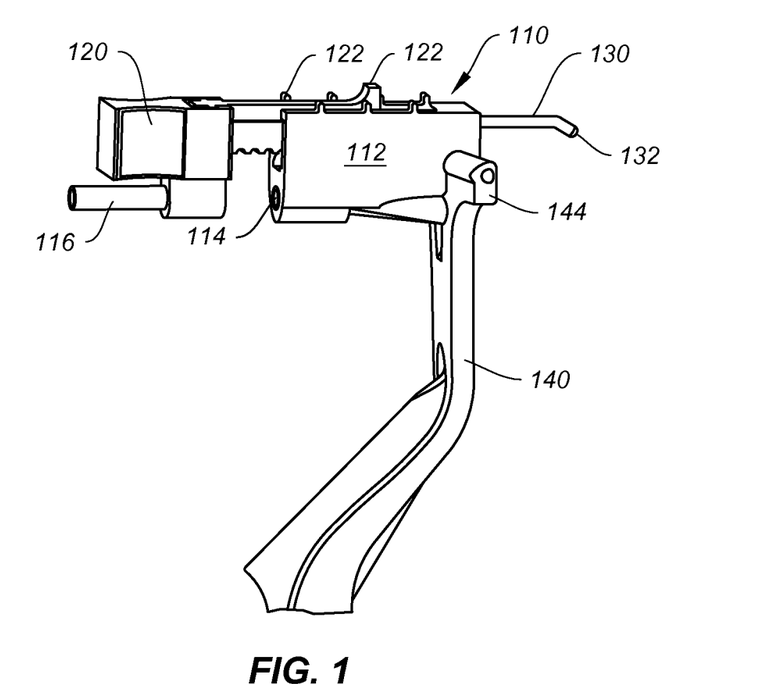
FIG. 1 is a perspective view of an exemplary embodiment of a guide instrument of the present disclosure.

FIG. 1 shows an exemplary embodiment of a guide instrument 100 of the present disclosure. The guide instrument 100 may comprise two interconnecting and detachable components: a cartridge, or housing, 110 and a handle 140. As shown in greater detail in FIG. 2, the housing 110 may comprise a main body 112 within which is contained an adjustable arm 120 that sits within and is translatable within the main body 112. The adjustable arm 120 can extend into a probe for visual targeting, such as for example, for use as an arthroscopic probe 130. The probe can extend into a tip 132 for resting against an articular surface of a bone of a joint. The guide instrument 100 may allow an access device or pin 250, such as the one shown in FIG. 3, to be drilled into bone to a depth that corresponds to this arthroscopic probe 130.

Figure 3:
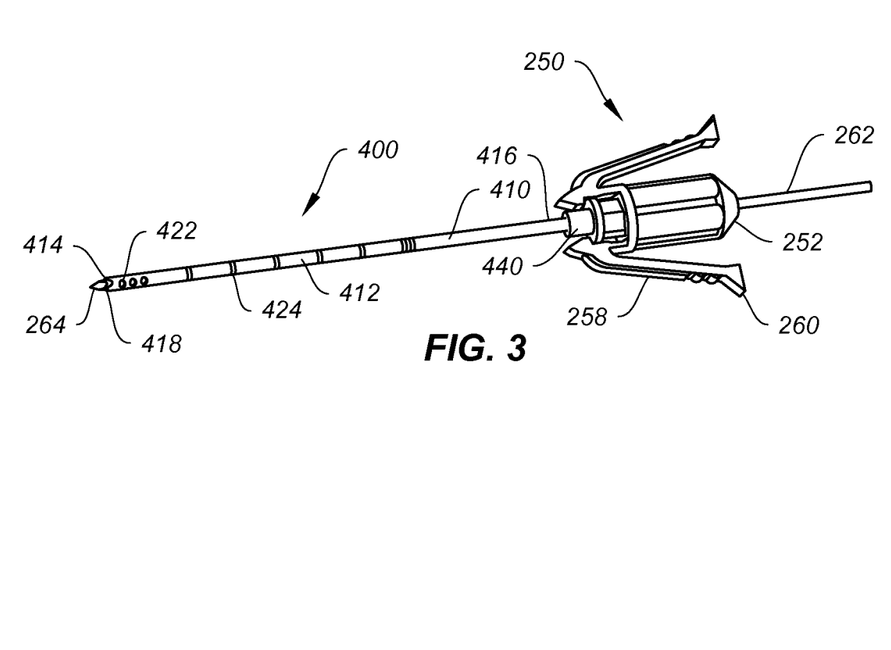
FIG. 3 shows an exemplary combined access device and adapter suitable for use with the guide instrument of FIG. 1.

FIG. 3 illustrates an exemplary connector 250 and access device and adapter 400 useful for targeting a subchondral region of the bone 2. The connector and access device and adapter 400 is similar to the type described in co-owned and co-pending U.S. patent application Ser. No. 13/854,796, entitled "SURGICAL ACCESS SYSTEMS, INSTRUMENTS AND ACCESSORIES," which was filed on Apr. 1, 2013 and published as U.S. Patent Application Publication No. 2013/0261650. In one embodiment, the access device 410 may comprise a cannulated shaft 412 for the introduction or removal of material therethrough. The access device component 410 may further include a first leading end 414, a second trailing end 416, a tip 418, one or more fenestrations 422, and one or more etchings 424.

In an effort to give the surgeons more control, the embodiments provide an access device that can be drilled into a patient's body with better control of depth because no excessive force is needed, while allowing the device to be driven in straight. Once the device is in place, the access device can serve as a port for injection or withdrawal of materials from the patient's body. Additionally, the adapter allows for a way to connect the access device to another system, such as an injection or extraction system. For instance, once the access device 410 is in place, an adapter may be attached to the access device to adapt it to an injection/extraction system, such as a standard syringe or Luer lock that may be connected to a standard power tool. Alternatively, the adapter may be formed integral to the access device, if so desired. The adapter may accommodate various connectors to make the instrument system compatible with a variety of known surgical instruments and tools.

In another embodiment, the access device 410 can be provided with external threads to help anchor the access device 410 into bone tissue such as during a bone treatment procedure. These threads may also facilitate insertion and distraction of the access device 410 into or out of the patient. For instance, the threads may help to draw the access device 410 towards the target area of insertion as it is driven into the patient, similar to a pulling action. Likewise, the threads may also help draw the access device 410 away from the target area as it is removed from the patient, similar to a pushing action. Other surface features, such as surface roughenings, barbs, teeth, projections, spikes may also be used in the embodiments.

As shown, etchings 424 may be provided at various positions along the length of the shaft 412. These etchings 424 may be marked in various fashions, such as with colors or other graphics, to make them visible during use. In addition, the etchings 424 may comprise radiopaque material to make them identifiable under fluoroscopy or X-ray intra-operatively.

The access device 410 also includes an adapter component 440 that may be molded with a geometry that enables mating with the connector 250. For instance, the geometry of the adapter component 440 may mirror an internal geometry of the connector 250 to allow for the application of force to rotate and position the access device component 410. Collectively, the access device 410, which effectively serves as a cannula, pin or needle, along with this adapter component 440, forms the combined access device and adapter 400. In some embodiments, the adapter component 440 may be a separate component from the access device 410, or may be formed integral to the access device itself 410.

One function of the adapter 440 is to allow the access device 410 to bridge to another system, such as an extraction or injection system. For example, the adapter 440 may be configured to attach to a Luer lock for a syringe. Alternatively, the adapter 440 may comprise connection means, such as a friction fit, an interference fit, a snap fit, etc. The adapter 440 serves to connect an access device 410 to an instrument such as for example a power tool for driving the access device 410 directly into the patient's body. Presently, these types of Luer lock or other connection end adapters are provided as a unitary body with the access device. Appli-cants have discovered a system for providing separable and connectable adapters with access devices that allow the combination to be power driven into a patient's body. This system thus allows the user to remove the adapter once the access device is inserted, without disturbing the rest of the access device 410.

As shown in FIG. 3, in one embodiment, the connector 250 may comprise a main body or cap 252, a pair of wings 258 having notched ends 260, and a central stem 262 provided through the main body 252. FIG. 3 shows the connector 250 fully inserted into the combined access device and adapter 400. During use, the stem 262 is inserted through the connector 250 and into the central channel of the access device component 410. The stem 262 aligns the connector 250 over the adapter component 440. The connector 250 is then slid over the stem 262 and placed over the overmolded adapter component 440. Once fully over the adapter component 440, the notched ends 260 may snap in place, and grab onto the adapter component 440. The notched ends 260 may be unsnapped by pressing the wings 258 inwards towards the main body 252, releasing the notched ends 260 from its snapped on position.

Figure 4:
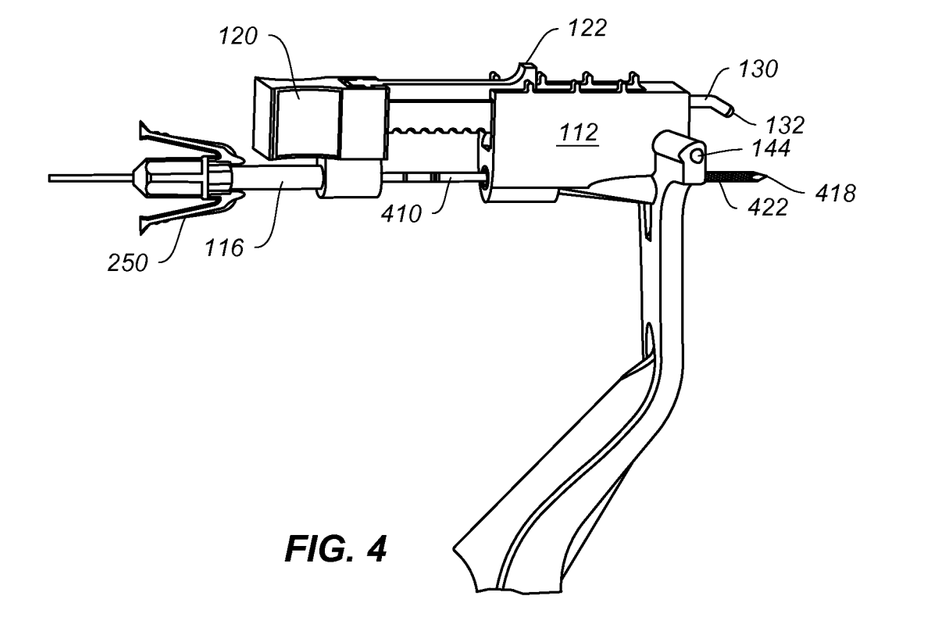
FIGS. 4 and 5 show a method of using the guide instrument of FIG. 1 with another exemplary embodiment of a combined access device and adapter.
Figure 5:
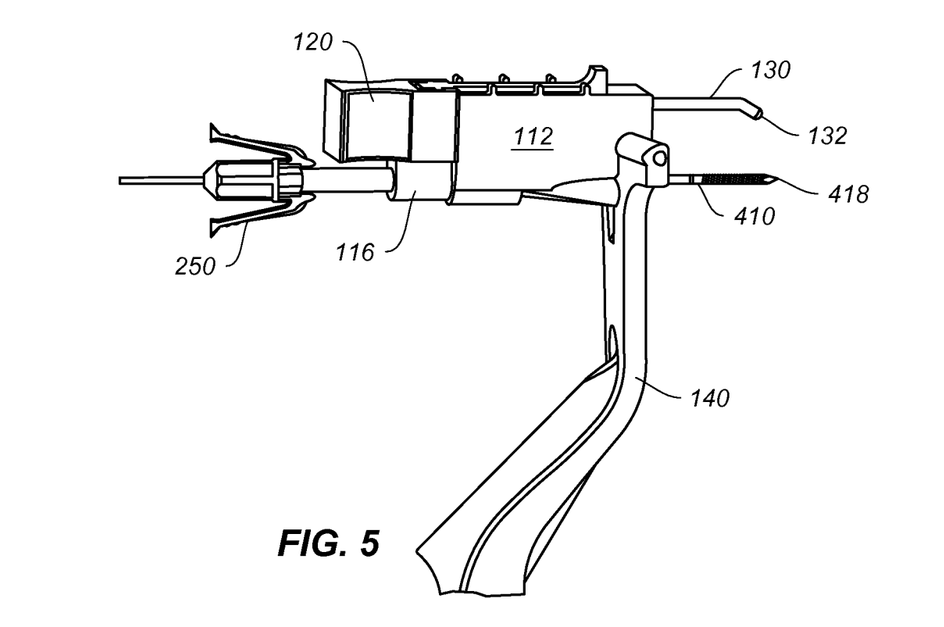
Figure 6:
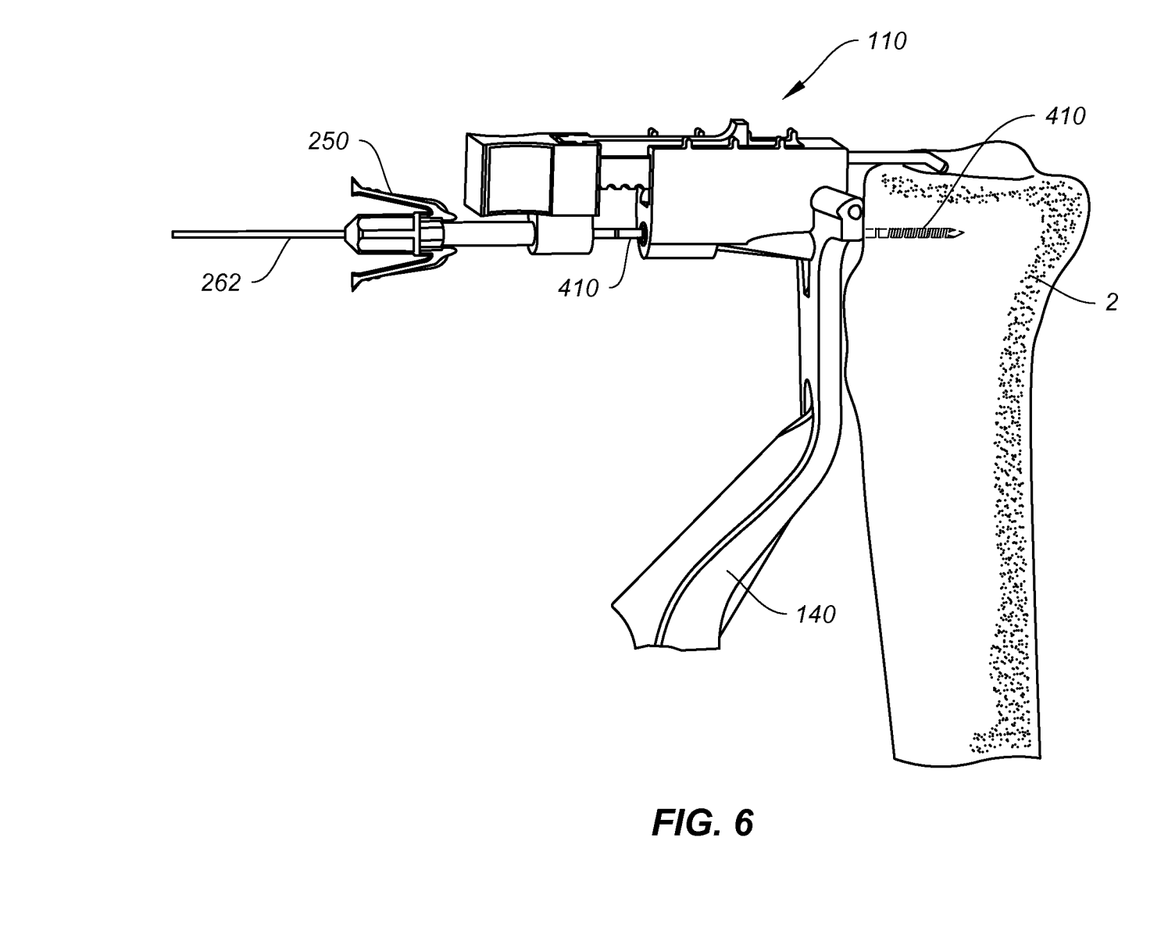
FIG. 6 shows the guide instrument of FIGS. 4 and 5 delivering the combined access device and adapter to a bone of a joint.

The shaft 412 of the access device component 410 may terminate in a first leading end 414 that is open. This open end 414 allows the sharp tip 264 of the central stem 262 of the connector 250 to extend through, thereby creating a sharp tip for entry of the combined devices into the patient. If so desired, the open end 414 may also be shaped so as to have sharp edges or projections for more secure engagement. In one embodiment, the sharp tip 264 of the central stem 262 may be configured as a closed trocar tip similar to side-targeted cannula devices. When the central stem 262 is placed through the shaft 412 of the combined access device and adapter 400, the fenestrations 422 may be closed off, as can be seen in FIG. 3. Removal of the central stem 262 would therefore allow the fenestrations 422 to be open to either inject or extract, as desired. As illustrated, in some embodiments, the stem may terminate in a sharp tip 264 to make it suitable for piercing bone or other tissue. In other embodiments, as shown in FIGS. 4 to 6, the access device 410 may have a closed tip 418 such that the stem 262 would reside within but not extend out of the access device tip 418.

It is fully understood that he embodiment shown in FIG. 3 is merely one example of the type of tools, instruments and accessories that are suitable for use with the guide instrument of the present disclosure. Additional access devices, along with adapter and connect components of a system of instruments, that may be used with the guide instrument 100 disclosed herein can be found in co-owned and co-pending U.S. patent application Ser. No. 13/854,796, entitled "SURGICAL ACCESS SYSTEMS, INSTRUMENTS AND ACCESSORIES," filed on Apr. 1, 2013 and published as U.S. Patent Application Publication No. 2013/0261650. Of course, other known and available access devices, including standard cannulas, trocars, pins, needles, and similar surgical access devices can also be used with the present guide instrument 100.

Figure 2:
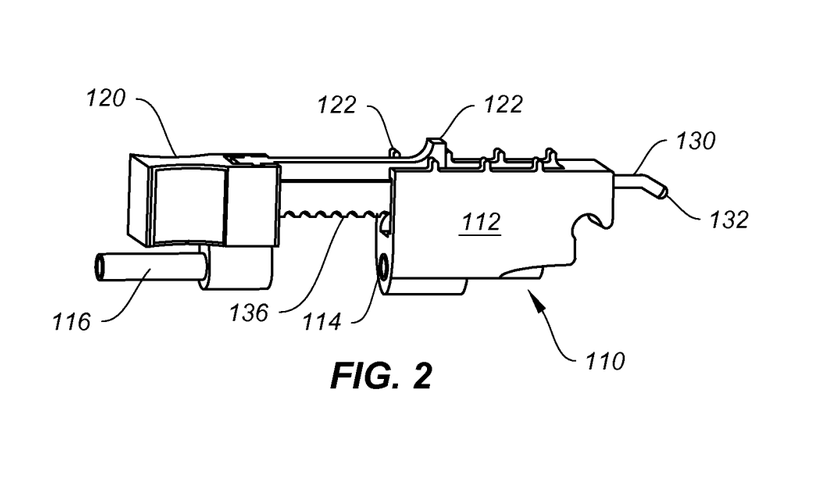
FIG. 2 is an enlarged view of the main body of the guide instrument of FIG. 1.

Turning back to the guide instrument 100 of the present disclosure and FIGS. 2 and 3, the probe 130 and its tip 132 and may be shaped to be easily accepted by the target joint and reach any point in the joint space. In use, the probe tip 132 may rest above bone, as shown in use in FIG. 6, though it is contemplated that the probe tip 132 may also rest on cartilage or a meniscus. For example, as shown in situ in FIG. 6, the probe tip 132 may rest on the tibial plateau of the tibial bone 2.

In other embodiments, however, the probe may not require a tip. Rather, the probe 130 itself may comprise a wire (such as, for example, an 18 gauge wire) or a needle or trocar. In such cases, the terminal end of the probe would serve the same function as the tip 132, for visual targeting. In other embodiments, the probe 130 may also be removable from the adjustable arm 120.

As shown, the adjustable arm 120 can include a port 116 for receiving an access device or pin 410 such as the ones described hereinabove. The port 116 aligns with an opening 114 in the main body 112 to allow the pin 410 to extend through and out of the main body 112. The adjustable arm 120 may include a ratcheting mechanism such as teeth 136, as shown in FIG. 2, to allow incremental movement of the adjustable arm 120 relative to the main body 112. Other translation and securement mechanisms can also be employed, such as a threaded system or a slide with cam system, to name a few examples.

Visual depth gauges 122 may be provided on the exterior surface of the adjustable arm 120 as well as on the main body 112, as shown. These gauges 122 may be provided as tabbed projections. Alignment of the tabbed projections would allow the user to determine the depth of the access device and adapter 400 relative to the probe 130. Further these visual markers provide feedback to the surgeon concerning depth. The ability to accurately target an internal location of the bone is critical to the success of many bone treatments, including SUBCHONDROPLASTY™ or SCP™ techniques. Accordingly, the guide instrument 100 of the present disclosure is helpful in providing even better clinical results by allowing greater depth control of the insertion or removal of materials into or out of bone.

In one embodiment, the housing 110 may be attached to a handle 140. The handle 140 may further include one or more fluoroscopic markers 144. The fluoroscopic markers 144 may correspond to anatomical markers, or serve as feedback to the surgeon. The handle 140 may be configured to rest against the patient's body, such as against the skin, bone or cartilage. In addition, the handle 140 may be configured to be pinned or secured to the patient's body during use. In some embodiments, the handle 140 may include a portal for receiving other additional access devices.

Movement of the adjustable arm 120 allows movement of the probe tip 132 with respect to the handle 140. By movement, what is meant is either rotation or other translation. In one example, the probe tip 132 may be shifted to rest above a desired position in the joint while the handle 140 remains in a fixed position relative to the patient's leg.

In use, the injection pin or access device 410 and its openings 422 would be fixed relative to the probe tip 132 once the pin (which has a fixed length) is full drilled into the bone 2 as a result of varying depth control. The proximal openings or fenestrations 422 of the access device or pin 410 may be predesigned to dock before, below, or past the probe tip 132. Accordingly, the pin or access device 410 is fully drilled in once it buttresses up against the instrument 100.

Some of the advantages this arthroscopic guide instrument 100 provides are the combination of a handle with means for resting firmly against the patient's leg, optionally with radiopaque markers that can be used to align with the tibia, and an articular probe that indexes and moves slidably with respect to the handle against the leg surface. In addition, the probe mechanism may comprise an open portal and depth control sleeve that is fixed relative to the targeting end of the probe to accept an access device or cannula of fixed length. As the probe tip 132 is indexed and adjusted with respect to the handle at any depth into the joint, the mechanism with portal depth control ensures that the maximum depth of the cannula is referenced and controlled with respect to the probe target end for any given indexed depth position of the probe.

FIGS. 4 to 6 represent an exemplary method of using the arthroscopic guide instrument 100 with a combined access device and adapter 400 similar to the one described above and illustrated in FIG. 3. In the present embodiment, the access device 410 may have a closed tip 418, as shown. Further, the tip 418 may also be a sharp tip for piercing tissue. Initially, the guide instrument 100 would rest against the patient's body and have an extendable/retractable probe 130. In surgery, the probe tip 132 could be positioned above the cartilage of a bone 2 believed to have a subchondral defect such as a lesion or edema. The cartilage may or may not show signs of damage. The instrument 100 may or may not be secured to the body before an access device 410 is drilled in through the port 116 and opening 114 of the housing 110.

The access device 410 is advanced into bone 2 until it buttresses up against the instrument 100. At that point, the tip of the pin or access device 410 would rest below the probe tip 132, regardless of whether the probe 130 is extended or retracted. The relative position could be, for example, where the tip of the probe 132 is above the first, middle or last fenestration or opening 422 on the access device 410. The access device 410 may also have a different tip that would rest relative to the probe tip 132.

The description of the invention is provided to enable any person skilled in the art to practice the various embodiments described herein. While the present invention has been particularly described with reference to the various figures and embodiments, it should be understood that these are for illustration purposes only and should not be taken as limiting the scope of the invention.

There may be many other ways to implement the invention. Various functions and elements described herein may be partitioned differently from those shown without departing from the spirit and scope of the invention. Various modifications to these embodiments will be readily apparent to those skilled in the art, and generic principles defined herein may be applied to other embodiments. Thus, many changes and modifications may be made to the invention, by one having ordinary skill in the art, without departing from the spirit and scope of the invention.

A reference to an element in the singular is not intended to mean "one and only one" unless specifically stated, but rather "one or more." The term "some" refers to one or more. Underlined and/or italicized headings and subheadings are used for convenience only, do not limit the invention, and are not referred to in connection with the interpretation of the description of the invention. All structural and functional equivalents to the elements of the various embodiments of the invention described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

What is claimed is:

1. A guide system for guiding an access device into a bone, comprising:
   a cartridge comprising a main body and a translatable arm receivable in the main body for translating relative to the main body, the translatable arm including a portal for receiving an access device in alignment with an opening in the main body;

a probe extending from the translatable arm and translating with the arm; and an access device configured to extend through the portal and the opening in the main body;

wherein the translatable arm is translatable relative to the main body with a ratcheting mechanism, the ratcheting mechanism including a plurality of teeth extending from the translatable arm to allow incremental movement of the translatable arm relative to the main body.

2. The guide system of claim 1 further comprising a handle extending from the cartridge.

3. The guide system of claim 1, wherein the access device includes a cannulated section.

4. A guide instrument for guiding an access device into a bone of a joint, comprising:

a cartridge comprising a main body and a translatable arm receivable in a passage in the main body for translating relative to the main body, the translatable arm including a portal for receiving an access device in alignment with an opening in the main body so that the access device can extend through the portal and the opening;

a probe extending from the translatable arm by a fixed distance, wherein translation of the translatable arm causes a corresponding translation of the probe relative to the main body; and a handle extending from the cartridge.

5. The guide instrument of claim 4, wherein the guide instrument s operable to guide the access device to a location spaced from the probe.

6. The guide instrument of claim 4, wherein the probe further comprises a probe tip.

7. The guide instrument of claim 6, wherein the probe tip is configured to rest against bone or cartilage.

8. The guide instrument of claim 4, wherein the probe comprises a wire.

9. The guide instrument of claim 8, wherein the wire is detachable.

10. The guide instrument of claim 4, wherein the probe comprises a needle or trocar.

11. The guide instrument of claim 4, wherein the translatable arm is translatable relative to the main body with a ratcheting system, a threaded system or a sliding cam system.

12. The guide instrument of claim 11, wherein the translatable arm is lockable within the main body.

13. The guide instrument of claim 4, wherein the handle is detachable from the cartridge.

14. The guide instrument of claim 4, wherein the cartridge comprises visual markers for depth control.

15. The guide instrument of claim 4, wherein the handle comprises a visual marker.

16. The guide instrument of claim 4, wherein the guide instrument is sized and shaped for arthroscopic use.

17. The guide instrument of claim 4, wherein the handle provides a passage for receiving a second access device.

18. A guide system for guiding an access device into a bone, comprising:

a cartridge comprising:
a main body;
a translatable arm receivable in the main body for translating relative to the main body, the translatable arm including a portal for receiving an access device in alignment with an opening in the main body, wherein the translatable arm is lockable within the main body, and wherein the cartridge comprises visual markers for depth control;
a ratcheting mechanism operable to control translation of the translatable arm relative to the main body; and
a probe extending from the translatable arm by a fixed distance and adapted to be positioned adjacent to a soft tissue or bone surface, wherein translation of the translatable arm causes a corresponding translation of the probe relative to the main body; and an access device configured to extend through the portal and the opening in the main body such that, when the access device is fully seated within the portal, a tip of the access device is disposed at a known position relative to a tip of the probe.

19. The guide system of claim 18, further comprising a handle configured to extend from the cartridge.

* * * * *